(12) United States Patent
Ishizu

(10) Patent No.: US 12,431,241 B2
(45) Date of Patent: Sep. 30, 2025

(54) INFORMATION PROCESSING APPARATUS AND CONTROL METHOD

(71) Applicant: CANON KABUSHIKI KAISHA, Tokyo (JP)

(72) Inventor: Satoshi Ishizu, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 402 days.

(21) Appl. No.: 17/987,110

(22) Filed: Nov. 15, 2022

(65) Prior Publication Data

US 2023/0187065 A1 Jun. 15, 2023

(30) Foreign Application Priority Data

Dec. 15, 2021 (JP) .................. 2021-203604

(51) Int. Cl.
| | |
|---|---|
| *G16H 40/67* | (2018.01) |
| *G06F 3/04845* | (2022.01) |
| *H04L 65/80* | (2022.01) |
| *H04N 5/262* | (2006.01) |
| *H04N 23/667* | (2023.01) |

(52) U.S. Cl.
CPC ......... *G16H 40/67* (2018.01); *G06F 3/04845* (2013.01); *H04L 65/80* (2013.01); *H04N 5/2628* (2013.01); *H04N 23/667* (2023.01)

(58) Field of Classification Search
None
See application file for complete search history.

(56) References Cited

U.S. PATENT DOCUMENTS

| | | | |
|---|---|---|---|
| 2017/0041570 A1* | 2/2017 | Takahashi | ............ H04N 5/2628 |
| 2020/0020071 A1* | 1/2020 | Frey | .......................... G06T 3/10 |
| 2021/0072885 A1* | 3/2021 | Ranchal | ............. G06F 3/04847 |
| 2022/0248957 A1* | 8/2022 | Abdulwaheed | ........ G16H 50/20 |

FOREIGN PATENT DOCUMENTS

JP 2019-133270 A 8/2019

* cited by examiner

*Primary Examiner* — Duc Nguyen
*Assistant Examiner* — Assad Mohammed
(74) *Attorney, Agent, or Firm* — VENABLE LLP

(57) ABSTRACT

A physician-side information processing apparatus is capable of being switched among a plurality of modes. The plurality of modes include a first mode in which a patient and a physician converse, a second mode in which an image of the patient is captured, wherein the second mode transitions from the first mode, a third mode in which the processing is performed on an image of the patient, wherein the third mode transitions from the second mode, and a fourth mode in which an explanation is given to the patient using the processed image, wherein the fourth mode transitions from the third mode. In the second mode, an instruction for capturing an image of the patient is transmitted to a patient-side information processing apparatus, and in the third mode, the information is transmitted to the patient-side information processing apparatus.

10 Claims, 10 Drawing Sheets

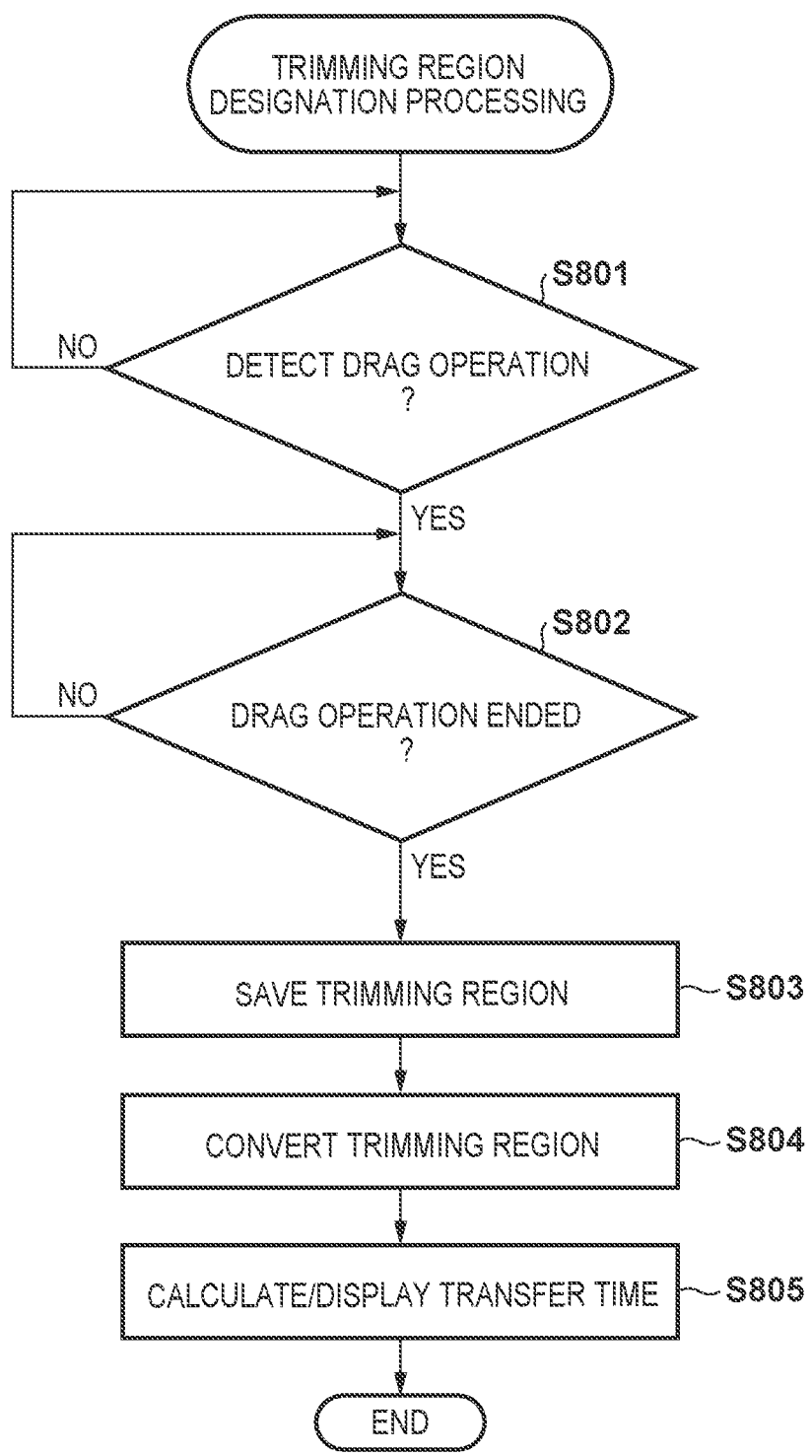

INFORMATION PROCESSING APPARATUS AND CONTROL METHOD

BACKGROUND OF THE INVENTION

Field of the Invention

The present invention relates to a system for supporting telemedicine.

Description of the Related Art

In a conventional telemedicine system, a physician performs an examination, considering expression and complexion of a patient and the contents of questions, while the physician side and the patient side view images of each other and have a conversation. In addition, although conventional telemedicine systems are provided with a user interface (UI) that is primarily intended for one-on-one conversations between a physician and a patient, they have not been provided with a UI that is suitable for examinations other than those in which one-on-one conversations are held. Japanese Patent Laid-Open No. 2019-133270 describes that, in a case of telemedicine, a UI displays an image of a medical specialist in addition to an image of a physician and an image of a patient.

However, Japanese Patent Laid-Open No. 2019-133270 does not provide a UI that conforms to a flow of an examination, such as image capturing of a patient (a diseased part) and explanation of the captured images, which are performed during the examination, in telemedicine that involves image capturing. In addition, there is a possibility that it may no longer be possible to perform smooth communication due to a physician being distracted by UI operation or displaying of images and UIs being delayed or disturbed by insufficient capacity or the like during communication.

SUMMARY OF THE INVENTION

The present invention has been made in consideration of the aforementioned problems, and realizes techniques for allowing display of images and UIs without delay or disturbance, thereby allowing smooth communication in telemedicine that involves image capturing.

In order to solve the aforementioned problems, the present invention provides a physician-side information processing apparatus that is connected so as to be capable of communicating with a patient-side information processing apparatus, the physician-side information processing apparatus comprising: a reception unit that receives from the patient-side information processing apparatus a second image in which a patient has been captured in response to an instruction of the physician-side information processing apparatus and whose data amount has been reduced in comparison to a first image in which the patient has been captured; a processing unit that performs processing for cutting out a partial image from the second image; and a transmission unit that transmits, to the patient-side information processing apparatus, information that has been set by performing the processing on the second image by the processing unit, wherein the reception unit receives from the patient-side information processing apparatus a processed image that is the first image on which the processing has been performed based on the information in the patient-side information processing apparatus.

In order to solve the aforementioned problems, the present invention provides a patient-side information processing apparatus that is connected so as to be capable of communicating with a physician-side information processing apparatus, the patient-side information processing apparatus comprising: a generation unit that generates a second image whose data amount has been reduced in comparison to a first image that has been generated by capturing a patient in response to an instruction of the physician-side information processing apparatus; a transmission unit that transmits to the physician-side information processing apparatus the second image; and a reception unit that receives, from the physician-side information processing apparatus, information that has been set by performing processing for cutting out a partial image from the second image in the physician-side information processing apparatus, wherein the transmission unit transmits to the physician-side information processing apparatus a processed image that is the first image on which the processing has been performed based on the information.

In order to solve the aforementioned problems, the present invention provides a method of controlling a physician-side information processing apparatus that is connected so as to be capable of communicating with a patient-side information processing apparatus, the method comprising: receiving from the patient-side information processing apparatus a second image in which a patient has been captured in response to an instruction of the physician-side information processing apparatus and whose data amount has been reduced in comparison to a first image in which the patient has been captured; performing processing for cutting out a partial image from the second image that is being displayed on the display unit; transmitting, to the patient-side information processing apparatus, information that has been set by performing the processing on the second image; and receiving from the patient-side information processing apparatus a processed image that is the first image on which the processing has been performed based on the information in the patient-side information processing apparatus.

In order to solve the aforementioned problems, the present invention provides a method of controlling a patient-side information processing apparatus that is connected so as to be capable of communicating with a physician-side information processing apparatus, the method comprising: generating a second image whose data amount has been reduced in comparison to a first image that has been generated by capturing a patient in response to an instruction of the physician-side information processing apparatus; transmitting to the physician-side information processing apparatus the second image; receiving, from the physician-side information processing apparatus, information that has been set by performing processing for cutting out a partial image from the second image in the physician-side information processing apparatus; and transmitting to the physician-side information processing apparatus a processed image that is the first image on which the processing has been performed based on the information.

In order to solve the aforementioned problems, the present invention provides a non-transitory computer-readable storage medium storing a program for causing a processor to function as a physician-side information processing apparatus that is connected so as to be capable of communicating with a patient-side information processing apparatus, the physician-side information processing apparatus comprising: a reception unit that receives from the patient-side information processing apparatus a second image in which a patient has been captured in response to an instruction of the physician-side information processing apparatus and whose data amount has been reduced in comparison to a first image in which the patient has been captured; a processing unit that performs processing for cutting out a partial image from the second image; and a transmission unit that transmits, to the patient-side information processing apparatus, information that has been set by performing the processing on the second image by the processing unit, wherein the reception unit receives from the patient-side information processing apparatus a processed image that is the first image on which the processing has been performed based on the information in the patient-side information processing apparatus.

In order to solve the aforementioned problems, the present invention provides a non-transitory computer-readable storage medium storing a program for causing a processor to function as a patient-side information processing apparatus that is connected so as to be capable of communicating with a physician-side information processing apparatus, the patient-side information processing apparatus comprising: a generation unit that generates a second image whose data amount has been reduced in comparison to a first image that has been generated by capturing a patient in response to an instruction of the physician-side information processing apparatus; a transmission unit that transmits to the physician-side information processing apparatus the second image; and a reception unit that receives, from the physician-side information processing apparatus, information that has been set by performing processing for cutting out a partial image from the second image in the physician-side information processing apparatus, wherein the transmission unit transmits to the physician-side information processing apparatus a processed image that is the first image on which the processing has been performed based on the information.

According to the present invention, images and UIs can be displayed without delay or disturbance and smooth communication can be performed in telemedicine that involves image capturing.

Further features of the present invention will become apparent from the following description of exemplary embodiments (with reference to the attached drawings).

BRIEF DESCRIPTION OF THE DRAWINGS

FIG. 8 is a flowchart illustrating storage region designation processing in step S712 of FIG. 7A.

DESCRIPTION OF THE EMBODIMENTS

Figure 1:
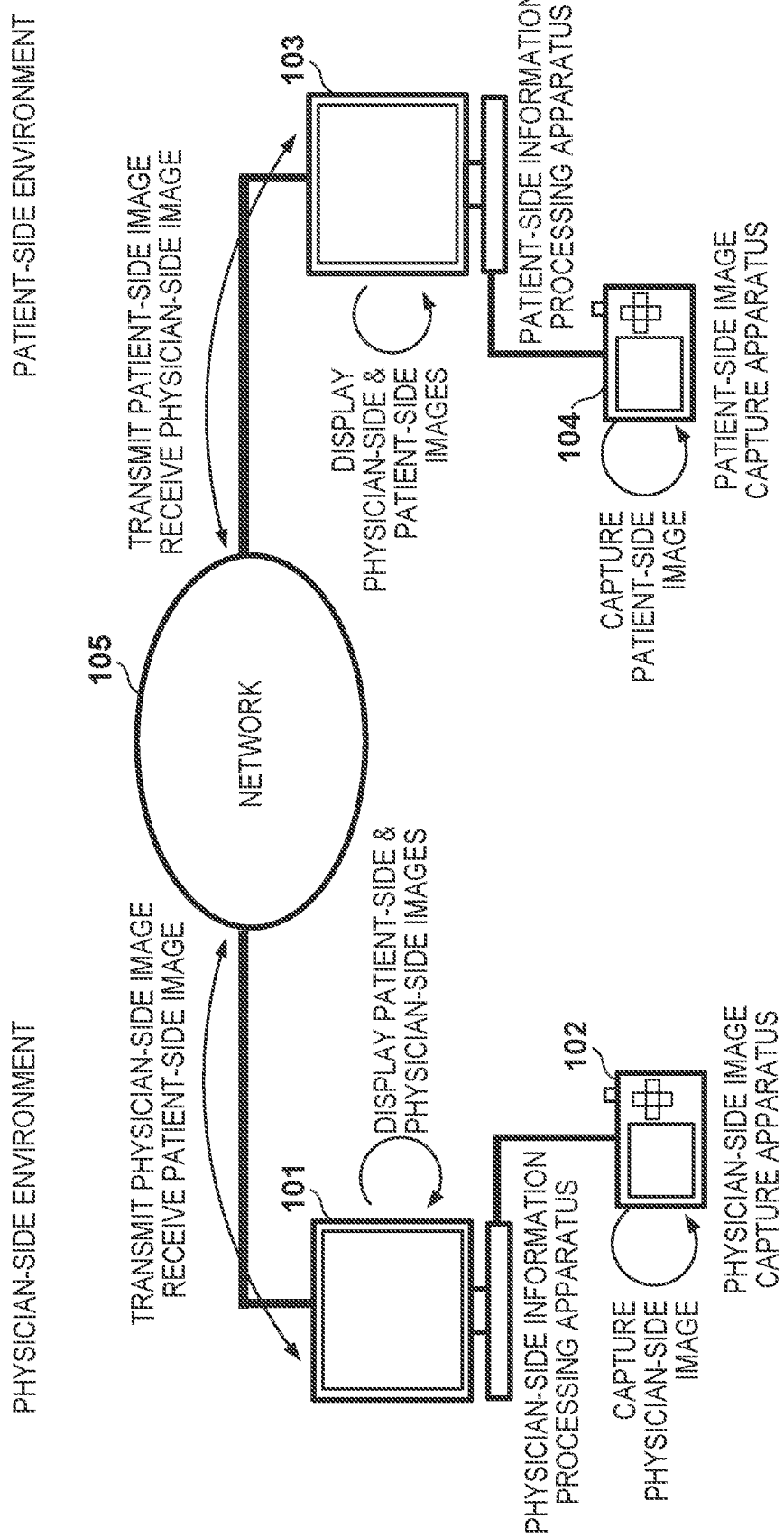
FIG. 1 is a system configuration diagram of the present embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

First Embodiment

Hereinafter, a description will be given for an embodiment in which the present invention has been applied to a system for supporting telemedicine (online examination) in which a physician-side information processing apparatus and a patient-side information processing apparatus are connected so as to be able to communicate via a network.
<System Configuration>

First, a system configuration of the present embodiment will be described with reference to FIG. 1.

Regarding the system of the present embodiment (hereinafter, the telemedicine system), a physician-side information processing apparatus, which is used by a physician in a medical facility such as a hospital, and a patient-side information processing apparatus, which is used by a patient in a residential facility such as a home or a care facility, are connected so as to be able to communicate via a network such as the Internet, and communication by voice or chat is possible using functions of an application that operates on the information processing apparatuses.

Further, the telemedicine system of the present embodiment includes a physician-side image capture apparatus for generating physician-side images and a patient-side image capture apparatus for capturing patient-side images and can perform communication more smoothly by the physician-side information processing apparatus and the patient-side information processing apparatus transmitting and receiving the physician-side images and the patient-side images via the network.

Regarding the telemedicine system of the present embodiment, a description will be given for an example of a configuration in which the physician-side image capture apparatus and the patient-side image capture apparatus generate images and the physician-side information processing apparatus and the patient-side information processing apparatus distribute the images; however, the present invention is not limited to this. For example, the physician-side information processing apparatus and the patient-side information processing apparatus may be provided with a function of an image capture apparatus. A communication form may be either wired or wireless. Regarding the network, a description will be given for an example of connecting a medical facility and a residential facility; however, it may be a closed intranet that is within a medical facility.

As illustrated in FIG. 1, a telemedicine system 100 of the present embodiment includes a physician-side information processing apparatus 101, a physician-side image capture apparatus 102, a patient-side information processing apparatus 103, and a patient-side image capture apparatus 104, and the physician-side information processing apparatus 101 and the patient-side information processing apparatus 103 are connected so as to be able to communicate via a network 105.

The physician-side information processing apparatus 101 is, for example, a desktop-type or notebook-type personal computer (PC) or a tablet PC. The patient-side information processing apparatus 103 is, for example, a desktop-type or notebook-type personal computer (PC), a tablet PC, a stick PC, or a smartphone. The physician-side and patient-side image capture apparatuses 102 and 104 are, for example, web cameras, compact cameras, or smartphones. The network 105 is, for example, the Internet, a wide area network (WAN), a local area network (LAN), or a public wireless communication network such as 4G or 5G. A method of communication between the physician-side information processing apparatus 101 and the patient-side information processing apparatus 103 is, for example, a peer-to-peer (P2P) type communication method, and communication is performed wirelessly or by cable. A method of communication between the physician-side information processing apparatus 101 and the physician-side image capture apparatus 102 is a wireless communication method, such as a wireless LAN, infrared communication, Bluetooth®, and a wireless USB; a public wireless communication method, such as 4G or 5G; or a wired communication method, such as a USB cable, HDMI®, and IEEE 1394. A method of communication between the patient-side information processing apparatus 103 and the patient-side image capture apparatus 104 is a wireless communication method, such as a wireless LAN, infrared communication, Bluetooth®, and a wireless USB; a public wireless communication method, such as 4G or 5G; or a wired communication method, such as a USB cable, HDMI®, and IEEE 1394.

The physician-side information processing apparatus 101 transmits physician-side data to the patient-side information processing apparatus 103 via the network 105. The physician-side image capture apparatus 102 generates image data, which includes a physician-side live view and other moving images and still images, and transmits it to the physician-side information processing apparatus 101. Further, the physician-side information processing apparatus 101 receives patient-side data from the patient-side information processing apparatus 103 via the network 105.

The physician-side data is, for example, data, such as characters and audio generated by the physician-side information processing apparatus 101, and image data generated by the physician-side image capture apparatus 102.

The patient-side information processing apparatus 103 transmits patient-side data to the physician-side information processing apparatus 101 via the network 105. The patient-side image capture apparatus 104 generates image data, which includes a patient-side live view and other moving images and still images, and transmits it to the patient-side information processing apparatus 103. Further, the patient-side information processing apparatus 103 receives physician-side data from the physician-side information processing apparatus 101 via the network 105.

The patient-side data is, for example, data, such as characters and audio generated by the patient-side information processing apparatus 103, and image data generated by the patient-side image capture apparatus 104.

With the above configuration, by the physician and the patient transmitting and receiving data to and from each other telemedicine can be performed.

<Apparatus Configuration>

Next, a configuration of an information processing apparatus and an image capture apparatus, which comprise the telemedicine system of the present embodiment, will be described with reference to FIG. 2.

Figure 2:
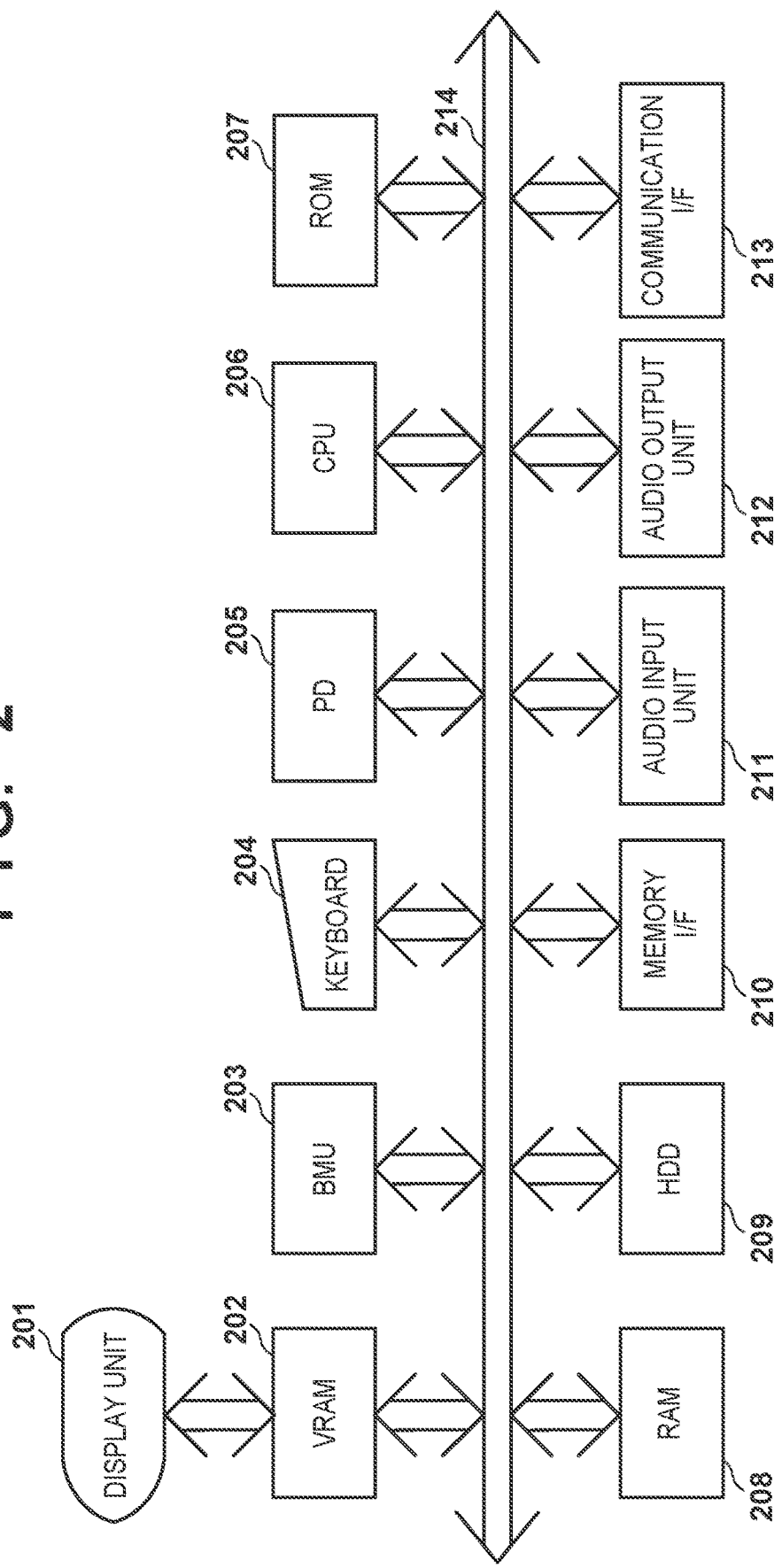
FIG. 2 is a block diagram illustrating an apparatus configuration of the present embodiment.

As illustrated in FIG. 2, the physician-side information processing apparatus 101, the patient-side information processing apparatus 103, the physician-side image capture apparatus 102, and the patient-side image capture apparatus 104 include a display unit 201, a VRAM 202, a BMU 203, a keyboard 204, a PD 205, a CPU 206, a ROM 207, a RAM 208, an HDD 209, a memory I/F 210, a microphone 211, a speaker 212, a communication I/F 213, and a bus 214.

The display unit 201 displays, for example, a live view and other images, icons, messages, and menus and other user interface information.

The VRAM 202 is a video memory in which data for display on the display unit 201 is rendered. The data rendered in the VRAM 202 is transferred to the display unit 201 in accordance with a predetermined specification, and thereby an image is displayed on the display unit 201.

The bit move unit (BMU) 203 is a circuit for controlling, for example, data transfer between memories (e.g., between the VRAM 202 and other memories) and data transfer between the memories and respective I/O devices (e.g., the communication I/F 213).

The keyboard 204 is an operation unit, which includes various keys for inputting characters and the like.

The pointing device (PD) 205 is used, for example, for indicating an icon, a menu, or other content that is displayed on the display unit 201 or for dragging and dropping an object.

The CPU 206 is a control unit that controls the respective devices based on an operating system (OS) and control programs (applications) that are stored in the ROM 207 and the HDD 209.

The ROM 207 is a non-volatile memory that stores control programs and data to be executed by the CPU 206.

The RAM 208 is a working memory, which includes a work area of the CPU 206, a data saving area at the time of error processing, a loading area for control programs, and the like.

The HDD 209 is an auxiliary storage apparatus that stores control programs, content, and data to be executed by the CPU 206.

The memory interface (I/F) 210 is a memory control unit that controls reading and writing of data from and to an external storage medium, such as a memory card.

The audio input unit 211 is one or more microphones that have been built into the apparatus or connected via an audio input terminal and generates audio signal that has been acquired by collecting sounds (audio) around the apparatus.

The audio output unit 212 is one or more speakers that have been built into the apparatus or connected via an audio output terminal and emits physician-side and patient-side audio and makes sounds, such as electronic sounds, in accordance with an operation state, instructions, and the like of the apparatus.

The communication I/F 213 is a communication unit that communicates with external apparatuses, such as an information processing apparatus and an image capture apparatus of a communication partner. Further, when an external apparatus is a communication device, such as a smartphone, the communication I/F 213 can perform public wireless communication, such as 4G and 5G communication.

The bus 214 includes an address bus, a data bus, and a control bus.

The control programs to be executed by the CPU 206 can be provided from the ROM 207, the HDD 209, and a memory card or from an external apparatus, which is connected via the communication I/F 213, and the like.

The control programs include an operating system (OS), which is basic software to be executed by the CPU 206, and applications, which cooperate with the OS to realize applied functions. The applications include an application for the physician-side information processing apparatus 101 and the patient-side information processing apparatus 103 of the present embodiment to execute processing of a flowchart, which will be described later.

The processing of the flowchart of the present embodiment is realized by reading software provided by an application. It is assumed that the application has software for utilizing the basic functions of the OSs installed on the physician-side information processing apparatus 101 and the patient-side information processing apparatus 103. The OSs of the physician-side information processing apparatus 101 and the patient-side information processing apparatus 103 may include software for realizing the processing in the present embodiment.

<Flow of Telemedicine and User Interface (UI)>

Next, a flow of telemedicine and UIs that conform to the flow of telemedicine of the present embodiment will be described with reference to FIG. 3.

Telemedicine that involves image capturing, for example, starts with conversations between a physician and a patient, a diseased part is captured, and diagnosis and explanation to the patient are performed using the captured image. At the end of the telemedicine, another conversation is had, and the examination is then ended. FIG. 3 describes a flow of telemedicine and UIs that conform to the flow of telemedicine.

In the following, the physician-side information processing apparatus 101 or the patient-side information processing apparatus 103 will be described as an executor of the processing; however, the processing is actually realized by the CPU 206 of the physician-side information processing apparatus 101 or the patient-side information processing apparatus 103 executing a program of a telemedicine application (or a function of the application, the OS, a service of the OS, and the like), which is stored in a storage unit. The same applies to FIGS. 4 to 8, which will be described later. The storage unit includes the ROM 207, the HDD 209, a memory card, an external apparatus connected via the communication I/F 213, and the like.

In step S301, the physician-side information processing apparatus 101 transmits to the patient-side information processing apparatus 103 an instruction for transitioning to a conversation mode. Further, the physician-side information processing apparatus 101 transmits a physician-side live view to the patient-side information processing apparatus 103, and the patient-side information processing apparatus 103 transmits a patient-side live view to the physician-side information processing apparatus 101.

The conversation mode is, for example, a mode in which a physician and a patient communicate, such as introducing oneself (ice breaking). In the conversation mode, the physician-side information processing apparatus 101 displays a UI 310 on the display 201. In the UI 310, a patient-side image, which has been acquired from the patient-side information processing apparatus 103, is displayed to be large. In the UI 310, a physician-side image 311 acquired by the physician-side image capture apparatus 102 is displayed superimposed on the lower left. This makes it possible for the physician to confirm how their image is being displayed on the patient side. Further, in the conversation mode, the patient-side information processing apparatus 103 displays a UI 312 on the display 201. In the UI 312, a physician-side image acquired from the physician-side information processing apparatus 101 is displayed to be large. In the UI 312, a patient-side image 313 acquired by the patient-side image capture apparatus 104 is displayed superimposed on the lower left.

In the conversation mode, when the physician inputs by voice an instruction for starting image capturing, for example, the physician-side information processing apparatus 101 determines that the voice, which has been obtained by the audio input unit 211, is an instruction for starting image capturing and transitions to an image capture mode of step S302. As a method other than voice, a configuration may be taken so as to dispose a mode change button in a UI that is displayed on the display 201 and when the physician-side information processing apparatus 101 determines that the mode change button has been operated by the PD 205, transition to the image capture mode of step S302.

In step S302, the physician-side information processing apparatus 101 transmits to the patient-side information processing apparatus 103 an instruction for transitioning to the image capture mode. Further, the patient-side information processing apparatus 103 transmits a thumbnail of an image of the patient (of a diseased part) captured by the patient-side image capture apparatus 104 to the physician-side information processing apparatus 101. The image capture mode is, for example, a mode for capturing a high-definition image of the patient (diseased part) that a physician needs for diagnosis. In the image capture mode, the physician-side information processing apparatus 101 displays a UI 320 on the display 201. In the UI 320, the image (thumbnail) of the patient (diseased part) acquired from the patient-side information processing apparatus 103 is displayed. Further, in the UI 320, an image capture start button 321 for executing processing for capturing an image of the patient (diseased part) is displayed superimposed on the lower right. Further, in the image capture mode, the patient-side information processing apparatus 103 displays a UI 322 on the display 201. In the UI 322, an image (original image) of the patient (diseased part) captured by the patient-side image capture apparatus 104 is displayed and the physician-side image 323 acquired from the physician-side information processing apparatus 101 is displayed superimposed on the lower right. This makes it possible to capture the diseased part that the physician wishes to capture and the diseased part that the patient wishes to be examined while they mutually confirm the diseased part in a large image.

In the image capture mode, an image of the patient (diseased part) is displayed to be large on both the display 201 of the physician-side information processing apparatus 101 and the display 201 of the patient-side information processing apparatus 103; however, the image quality of the thumbnail that is displayed on the display 201 of the physician-side information processing apparatus 101 may be deteriorated in comparison with the original image that is displayed on the display 201 of the patient-side information processing apparatus 103. This may be a result of compression processing at the time of streaming distribution, and as a countermeasure for such a deterioration in image quality, it is effective that the physician-side information processing apparatus 101 acquires the original image from the patient-side information processing apparatus 1103.

In the image capture mode, when the physician-side information processing apparatus 101 determines that the image capture start button 321 has been operated by the PD 205, for example, the physician-side information processing apparatus 101 transitions to a trimming mode of step S303. As a method other than a button operation, a configuration may be taken so as to transition to the trimming mode of step S303 when it is determined that a shutter button of the patient-side image capture apparatus 104 has been operated in the patient-side information processing apparatus 103.

In step S303, the physician-side information processing apparatus 101 transmits to the patient-side information processing apparatus 103 an instruction for transitioning to the trimming mode. The trimming mode is a mode for performing processing for cutting out a region that is part of an image of the patient (diseased part) and is necessary for diagnosis by the physician. Details of the trimming mode will be described later in FIGS. 4 and 8. In the trimming mode, the physician-side information processing apparatus 101 displays a UI 330 on the display 201. The UI 330 displays a thumbnail of an image of the patient (diseased part) captured in step S302. The thumbnail is acquired from the patient-side information processing apparatus 103 in the processing, which will be described later in FIGS. 7A-7C. Further, the UI 330 displays a cursor 332, which indicates an operation position of the PD 205, and a trimming region 331, which has been set by dragging the PD 205. Further, in the trimming mode, the patient-side information processing apparatus 103 displays a UI 333 on the display 201. In the UI 333, the image (original image) of the patient (diseased part) captured by the patient-side image capture apparatus 104 is displayed. Further, in the UI 333, a message 334, which represents that a trimming operation is in progress in the physician-side information processing apparatus 101, is displayed superimposed on the upper left and the physician-side image 335 acquired from the physician-side information processing apparatus 101 is displayed superimposed on the lower right. The physician-side image 335 is an image by which it can be seen that the physician is concentrating on the trimming operation. This makes it possible to clearly express in the UI that the physician is currently doing work for the examination and is in a state in which it is temporarily difficult to engage in communication.

The image (thumbnail) of the patient (diseased part) is trimmed not only to limit an image region to be explained to the patient in an explanation mode of step S305 to facilitate understanding of the patient but also to reduce the file size of the trimmed image to be transmitted to the patient-side information processing apparatus 103 to minimize the data transfer time and suppress image and audio disturbance due to stressing the communication bandwidth.

When the trimming operation is completed in the physician-side information processing apparatus 101, the physician-side information processing apparatus 101 and the patient-side information processing apparatus 103 start image transmission processing of step S304.

In step S304, the physician-side information processing apparatus 101 transmits information of the trimming region 331, which has been set in step S303, to the patient-side information processing apparatus 103. The patient-side information processing apparatus 103 generates based on the information of the trimming region 331 received from the physician-side information processing apparatus 101 a processed image (trimmed original image), which has been obtained by performing trimming processing on the original image, and transmits it to the physician-side information processing apparatus 101. The physician-side information processing apparatus 101 displays a UI 340 on the display 201 until the trimmed original image is received from the patient-side information processing apparatus 103. In the UI 340, a trimmed thumbnail 341 is displayed. When the trimmed original image is received from the patient-side information processing apparatus 103, the physician-side information processing apparatus 101 replaces the trimmed thumbnail 341 that is displayed on the UI 340 with a trimmed original image 342. This makes it possible to continue telemedicine without disturbance in the waiting time during reception of the trimmed original image. Further, in the UI 340, a patient-side image 343, which has been acquired from the patient-side information processing apparatus 103, is displayed. Further, in the image transmission processing of step S304, the patient-side information processing apparatus 103 displays a UI 344 on the display 201. In the UI 344, the trimmed original image 345, which has been obtained by trimming the original image based on the information of the trimming region 331 received from the physician-side information processing apparatus 101 in the patient-side information processing apparatus 103, is displayed. Further, in the UI 344, a message 346, which represents that the trimming operation in the physician-side information processing apparatus 101 has been completed, is displayed on the upper left.

The image transmission processing of step S304 corresponds to the processing during the transmission of the trimmed original image, which has been generated by the patient-side information processing apparatus 103, to the physician-side information processing apparatus 101, and in the UI, the explanation mode of step S305 is started in a few seconds.

In step S305, the physician-side information processing apparatus 101 transmits to the patient-side information processing apparatus 103 an instruction for transitioning to the explanation mode. Further, the physician-side information processing apparatus 101 transmits a physician-side live view to the patient-side information processing apparatus 103, and the patient-side information processing apparatus 103 transmits a patient-side live view to the physician-side information processing apparatus 101.

The explanation mode is a mode in which the physician explains the examination result and the like to the patient while referring to the trimmed original image, which has been generated by the patient-side information processing apparatus 103. In the explanation mode, the physician-side information processing apparatus 101 displays a UI 350 on the display 201 so that the physician and the patient can refer to the same trimmed original image. In the UI 350, a trimmed original image 351 which has been acquired from the patient-side information processing apparatus 103, a physician-side image 352 which has been acquired by the physician-side image capture apparatus 102, and a patient-side image 353 which has been acquired from the patient-side information processing apparatus 103 are displayed. Further, in the explanation mode, the patient-side information processing apparatus 103 displays a UI 354 on the display 201 so that the physician and the patient can refer to the same trimmed original image. In the UI 354, a trimmed original image 355 which has been generated by the patient-side information processing apparatus 103 is displayed, a patient-side image 356 which has been acquired by the patient-side image capture apparatus 104 is displayed on the lower left, and a physician-side image 357 acquired from the physician-side information processing apparatus 101 is displayed on the lower right. This makes it possible for the physician to explain to the patient and the patient to hear from the physician the state and the like of the diseased part while the physician and the patient refer to the same trimmed original image.

In the explanation mode, when the physician conveys by voice to the patient that they will end the explanation, for example, the physician-side information processing apparatus 101 determines that the voice, which has been acquired by the audio input unit 211, is an instruction for ending explanation and transitions to a conversation mode of step S306. As a method other than voice, a configuration may be taken so as to dispose an explanation end button in a UI that is displayed on the display 201 and when the physician-side information processing apparatus 101 determines that the explanation end button has been operated by the PD 205, transition to the conversation mode of step S306.

In the conversation mode of step S306, the physician-side information processing apparatus 101 and the patient-side information processing apparatus 103 transition to the conversation mode, which is the same as that of step S301. In the conversation mode of step S306, the physician and the patient converse on drugs to be prescribed, questions and answers on the entire examination, the next examination, and the like and end the telemedicine.

The display timings, positions, and sizes of the images 311, 321, 323, 335, 352, and 356 displayed superimposed on the UIs 310, 320, 340, and 350 of the physician-side information processing apparatus 101 and the images 313, 343, 353, and 355 displayed superimposed on the UIs 312, 322, 333, 344, and 354 of the patient-side information processing apparatus 103 can be controlled by setting in advance databases, setting values, and the like for each mode.

<Trimming Mode>

Next, the processing and a UI of the trimming mode in step S303 of FIG. 3 will be described with reference to FIG. 4.

Figure 3:
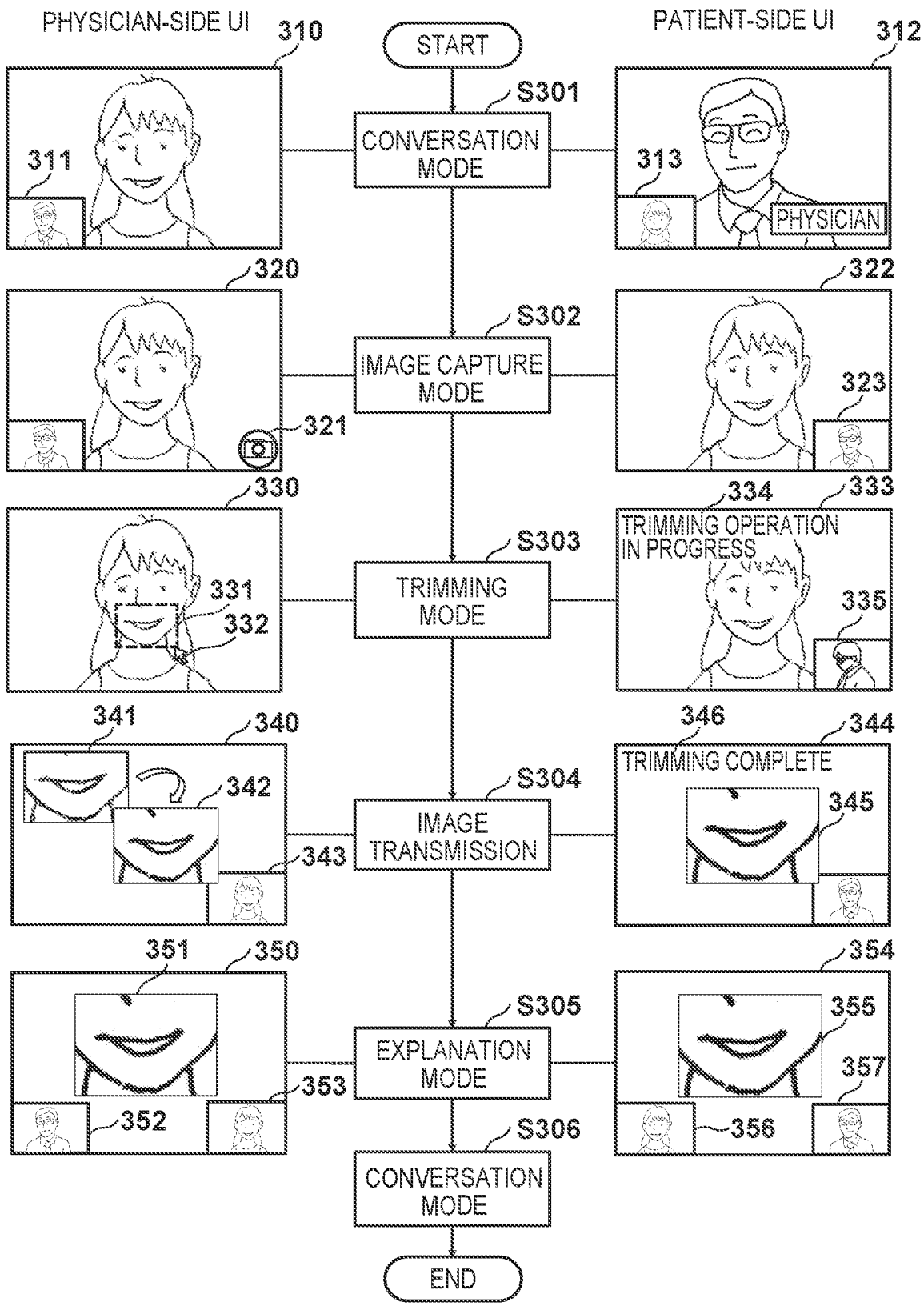
FIG. 3 is a diagram illustrating a flow of telemedicine and UIs that conform to the flow of telemedicine of the present embodiment.
Figure 4:
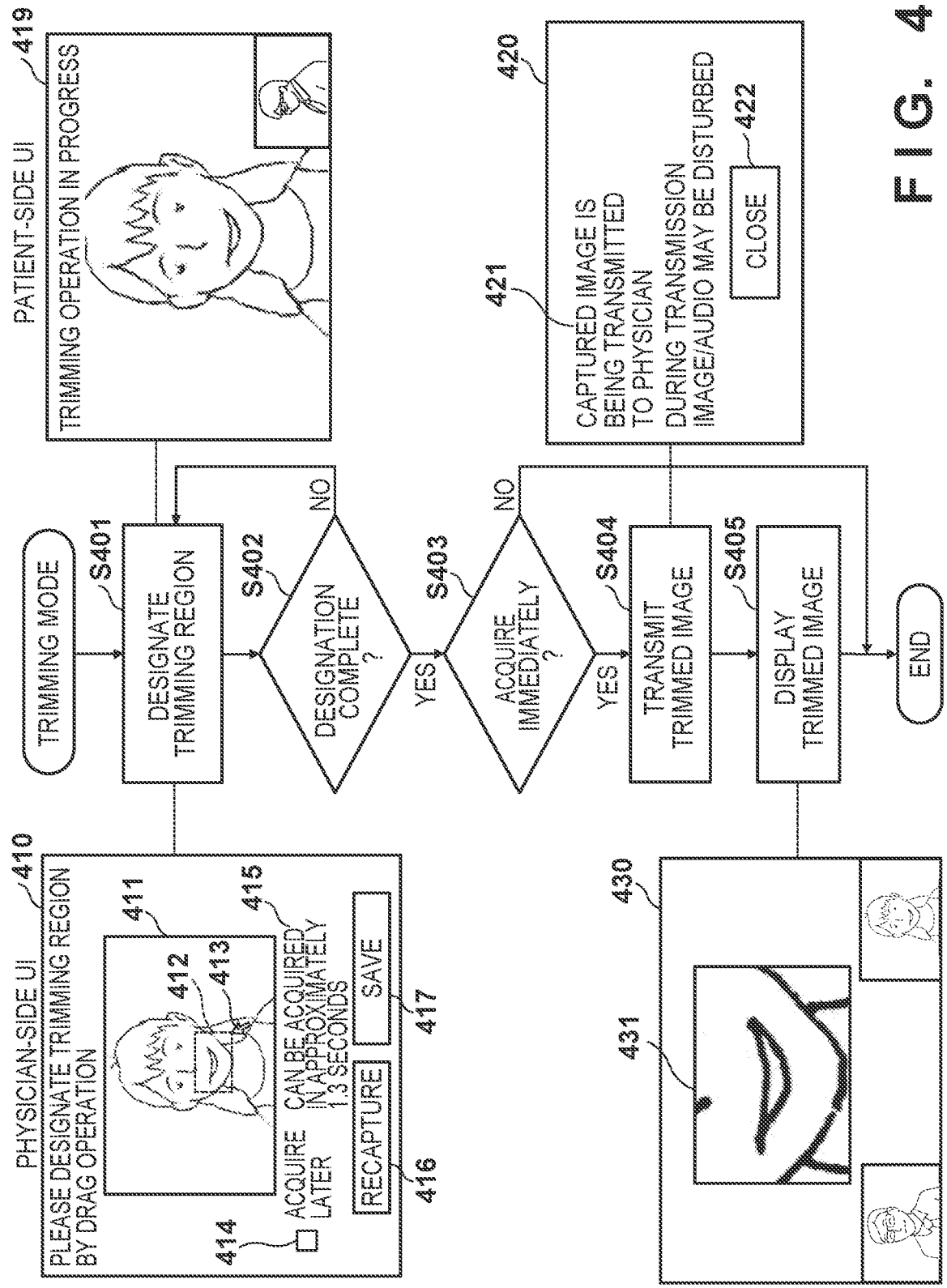
FIG. 4 is a diagram illustrating a flowchart and UIs in a trimming mode of the present embodiment.

FIG. 4 exemplifies a flowchart illustrating the processing of the trimming mode in step S303 of FIG. 3 and UIs. Details of the trimming processing will also be described in FIGS. 7 and 8.

When the trimming mode is started, the physician-side information processing apparatus 101 displays on the display 201 a UI 410, which includes a thumbnail 411 which has been acquired from the patient-side information processing apparatus 103 in the image capture mode of step S302 of FIG. 3. Further, in the UI 410, below the thumbnail 411, a check box 414, a transfer time display 415, an image re-capture button 416, and a save button 417 are displayed. The check box 414 can set the timing for acquiring trimmed original images from the patient-side information processing apparatus 103 and is checked when it is desired to collectively acquire them after the telemedicine of FIG. 3. The transfer time display 415 represents the time until the trimmed original image is received from the patient-side information processing apparatus 103. The image re-capture button 416 is operated when it is desired to discard and re-capture the image of the patient (the diseased part) due to camera shake or the like at the time of capturing by the patient-side image capture apparatus 104 in the image capture mode of step S302 of FIG. 3. The save button 417 is operated when determining the trimming region and transmitting the information of the trimming region to the patient-side information processing apparatus 103. Further, in the UI 410, a message 418, which represents that the trimming region can be designated by a drag operation of the PD 205, is displayed.

In step S401, the physician-side information processing apparatus 101 determines a drag operation position of the PD 205 in the UI 410 as an operation for specifying the trimming region of the thumbnail 411. Then, the physician-side information processing apparatus 101 displays a cursor 413, which indicates the operation position of the PD 205, and the trimming region 412, which corresponds to the dragging of the PD 205, superimposed on the thumbnail 411. This makes it possible for the physician to quickly specify the region of the diseased part that is needed for examination. The patient-side information processing apparatus 103 displays a UI 419 on the display 201. A description will be omitted for the UI 419 as it is the same as the UI 333 of FIG. 3.

In step S401, when the physician-side information processing apparatus 101 detects the drag operation by the PD 205 on the thumbnail 411, the physician-side information processing apparatus 101 starts the processing of step S402. Further, when the physician-side information processing apparatus 101 detects that the image re-capture button 416 has been operated by the PD 205, the physician-side information processing apparatus 101 starts the processing of the image capture mode of step S302 of FIG. 3.

In step S402, the physician-side information processing apparatus 101 determines whether or not the save button 417 has been operated by the PD 205. When the physician-side information processing apparatus 101 determines that the save button 417 has not been operated, the physician-side information processing apparatus 101 returns the processing to step S401 and waits until the designation of the trimming region is completed. When the physician-side information processing apparatus 101 determines that the save button 417 has been operated, the physician-side information processing apparatus 101 advances the processing to step S403. The transfer time display 415 displays the approximate time it takes for the physician to acquire the trimmed original image as a material for determining whether or not to operate the save button 417. The data transfer time varies depending on the size of the trimming region 412. As will be described later in FIG. 8, the data transfer time is calculated based on the data transfer rate or the like between the physician-side information processing apparatus 101 and the patient-side information processing apparatus 103.

In step S403, the physician-side information processing apparatus 101 determines the setting of the check box 414. When the physician-side information processing apparatus 101 determines that the check box 414 is checked, the physician-side information processing apparatus 101 advances the processing to step S404 and when the physician-side information processing apparatus 101 determines that the check box 414 is not checked, the physician-side information processing apparatus 101 ends the processing. Checking the check box 414 makes possible, for example, a setting for collectively transmitting trimmed original images after telemedicine has ended. This is useful, for example, when a trimmed original image is not used in the explanation mode of step S305 of FIG. 3 but is used for records and the like in electronic medical records.

In step S404, the patient-side information processing apparatus 103 generates a trimmed original image based on the information of a trimming region, which has been received from the physician-side information processing apparatus 101, and transmits it to the physician-side information processing apparatus 101. The physician-side information processing apparatus 101 receives the trimmed original image, which has been generated in the patient-side information processing apparatus 103. The processing of step S404 is the same as the image transmission processing of step S304 of FIG. 3. In step S404, the patient-side information processing apparatus 103 displays on the display 201 a dialog 420, which includes a message 421 and a close button 422. The message 421 is a character string, which notifies that there is a risk that a streaming image or audio will be disturbed. Regarding the close button 422, it is possible to hide the dialog 420 by operating the close button 422 by the PD 205 in the patient-side information processing apparatus 103. When the trimmed original image is transmitted from the patient-side information processing apparatus 103 to the physician-side information processing apparatus 101, the processing of step S405 is started.

In step S405, the physician-side information processing apparatus 101 displays on the display 201 a UI 430, which includes a trimmed original image 431 which has been acquired from the patient-side information processing apparatus 103, and terminates the processing. A description will be omitted for the UI 430 as it is the same as the UI 350 of FIG. 3.

<Modification of System Configuration>

Next, a modification of the system configuration of the present embodiment will be described with reference to FIGS. 5 and 6.

Figure 5:
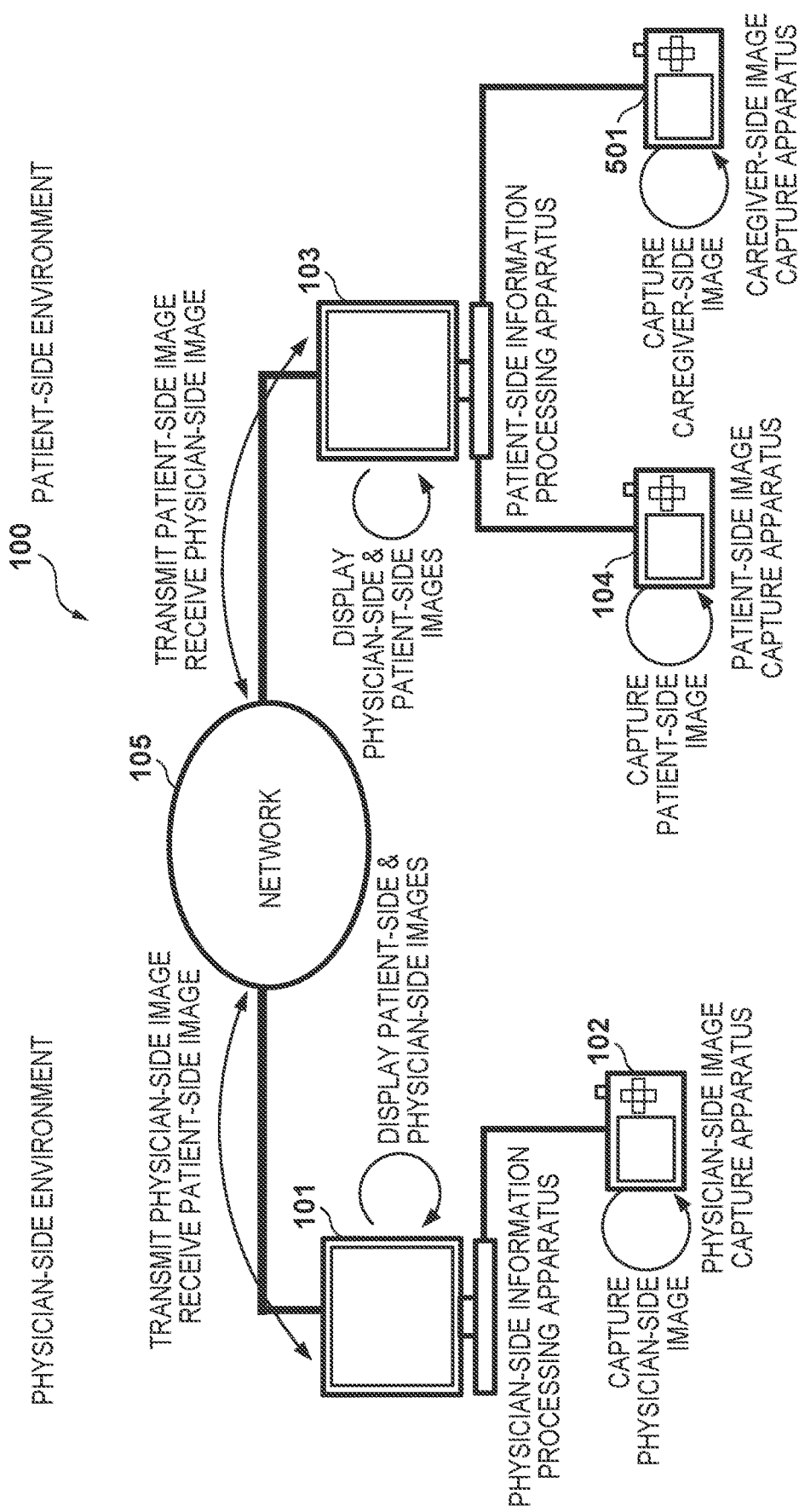
FIG. 5 is a diagram illustrating a modification of the system configuration of the present embodiment.

Regarding the system configuration of FIG. 5, a caregiver-side image capture apparatus 501 has been added to the patient-side information processing apparatus 103 with respect to the system configuration of FIG. 1. It is assumed that the caregiver-side image capture apparatus 501 is held, for example, by a caregiver (care person, nurse, and the like), who is a third party other than the patient. This makes it possible to capture images of the back, which cannot be captured by the patient alone, and the like, and by sharing them with the physician, it becomes possible to assist in telemedicine.

A method of communication between the patient-side information processing apparatus 103 and the caregiver-side image capture apparatus 501 is the same as the method of communication between the patient-side information processing apparatus 103 and the patient-side image capture apparatus 104.

Figure 6:
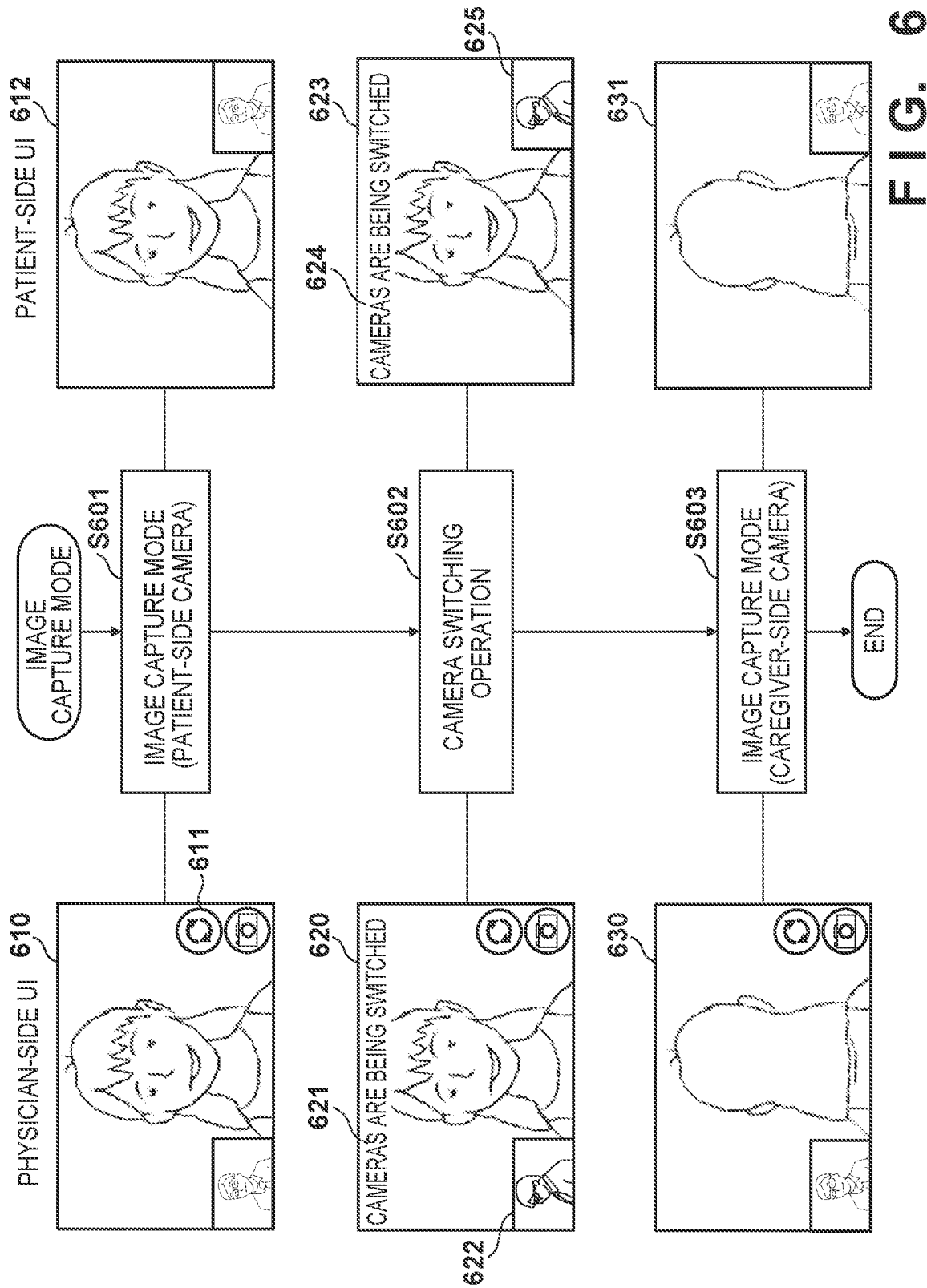
FIG. 6 is a diagram illustrating a flowchart and UIs in an image capture mode in the modification of the system configuration of the present embodiment.

FIG. 6 exemplifies a flowchart illustrating a flow of a modification of the image capture mode of FIG. 3 and UIs.

In step S601, the physician-side information processing apparatus 101 transmits to the patient-side information processing apparatus 103 an instruction for transitioning to the image capture mode. Step S601 is the same as the image capture mode of step S302 of FIG. 3. In the image capture mode of step S601, the physician-side information processing apparatus 101 displays a UI 610 on the display 201, for example. The patient-side information processing apparatus 103 displays a UI 612 on the display 201. Regarding the UI 610 of the physician-side information processing apparatus 101, a camera switching button 611 has been added to the UI 320 of the physician-side information processing apparatus 101 of FIG. 3. The camera switching button 611 is a button that allows the physician to select whether to capture the patient by the patient-side image capture apparatus 104 or to capture the patient by the caregiver-side image capture apparatus 501. The UI 612 of the patient-side information processing apparatus 103 is the same as the UI 322 of the patient-side information processing apparatus 103 of FIG. 3. When the physician-side information processing apparatus 101 determines that the camera switching button 611 has been operated by the PD 205, the physician-side information processing apparatus 101 starts the processing of step S602.

In step S602, the physician-side information processing apparatus 101 transmits to the patient-side information processing apparatus 103 an instruction for switching cameras. In response to the camera switching instruction which has been received from the physician-side information processing apparatus 101, the patient-side information processing apparatus 103 determines an image capture apparatus that is currently set as a device for performing image capturing among the patient-side image capture apparatus 104 and the caregiver-side image capture apparatus 501 and whether or not there is a currently-connected image capture apparatus that is not currently set as the device for performing image capturing. In the example of FIG. 5, when the patient-side image capture apparatus 104 is the currently-set image capture apparatus, the caregiver-side image capture apparatus 501 becomes a currently-connected image capture apparatus. The physician-side information processing apparatus 101 displays a UI 620 on the display 201. The patient-side information processing apparatus 103 displays a UI 623 on the display 201. In UIs 620 and 623, messages 621 and 624, which represent that the cameras are being switched in the patient-side information processing apparatus 103, are displayed superimposed on the upper left of the image of the patient (diseased part). In addition, in the UI 620, a physician-side image 622 is displayed superimposed on the lower left of the image of the patient (diseased part). In the UI 623, a physician-side image 625 is displayed superimposed on the lower right of the image of the patient (diseased part). The physician-side images 622 and 625 are images in which the physician is focused on a camera switching operation. This makes it possible to clearly express in the UI that the physician is currently performing a camera switching operation and is in a state in which it is temporarily difficult to engage in communication.

In step S603, the patient-side information processing apparatus 103 determines whether or not there is a currently-connected image capture apparatus other than the currently-set image capture apparatus in response to the camera switching instruction which has been received in step S602. When the patient-side information processing apparatus 103 determines that there is a currently-connected image capture apparatus, the patient-side information processing apparatus 103 switches the currently-set image capture apparatus to the currently-connected image capture apparatus, and when the patient-side information processing apparatus 103 determines that there is no currently-connected image capture apparatus, the patient-side information processing apparatus 103 ends the processing. In the example of FIG. 5, the currently-set image capture apparatus is switched from the patient-side image capture apparatus 104 to the caregiver-side image capture apparatus 501. The physician-side information processing apparatus 101 displays a UI 630 on the display 201. The patient-side information processing apparatus 103 displays a UI 631 on the display 201. In the UIs 630 and 631, the image of the patient (diseased part), which has been captured by the image capture apparatus after changing the currently-set image capture apparatus, is displayed. In the example of FIG. 5, the image of the patient (diseased part) captured by the caregiver-side image capture apparatus 501 is displayed. Thus, examination can be performed by switching an image in which the patient is captured from the front to an image that is captured from the back, from the viewpoint of an assistant, for example, and sharing it with the physician.

The camera switching button 611 may be disposed on the UI of the patient-side information processing apparatus 103, and the currently-connected image capture apparatus may be changed every time the camera switching button 611 is operated. Furthermore, the camera switching button 611 may be of a menu display format for selecting the name and unique identification information (MAC address and the like) of the currently-connected image capture apparatus.

<Operation Flow>

Figure 7A:
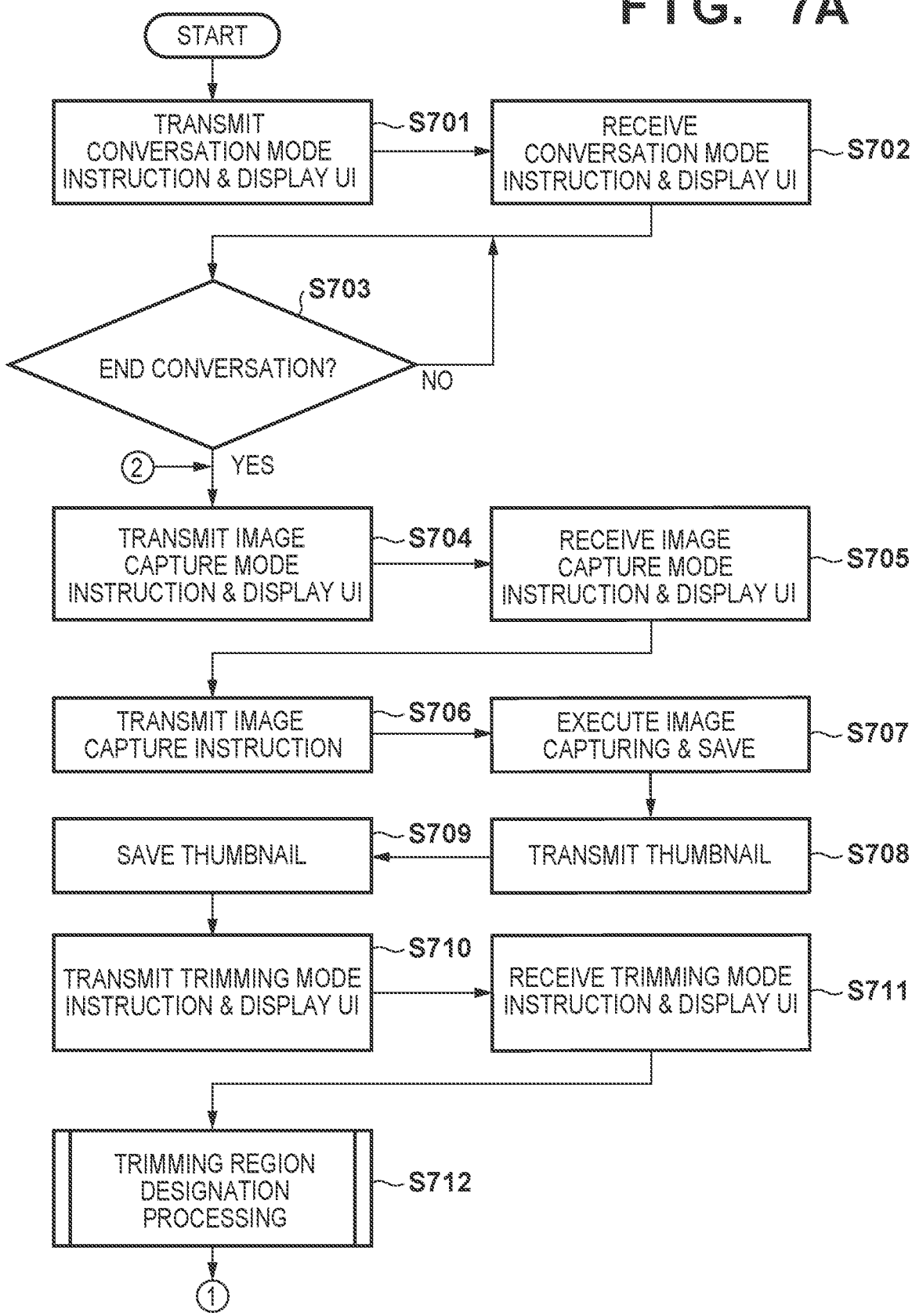
FIGS. 7A-7C are flowcharts illustrating an operation of a physician-side information processing apparatus and a patient-side information processing apparatus in a telemedicine system of the present embodiment.
Figure 7B:
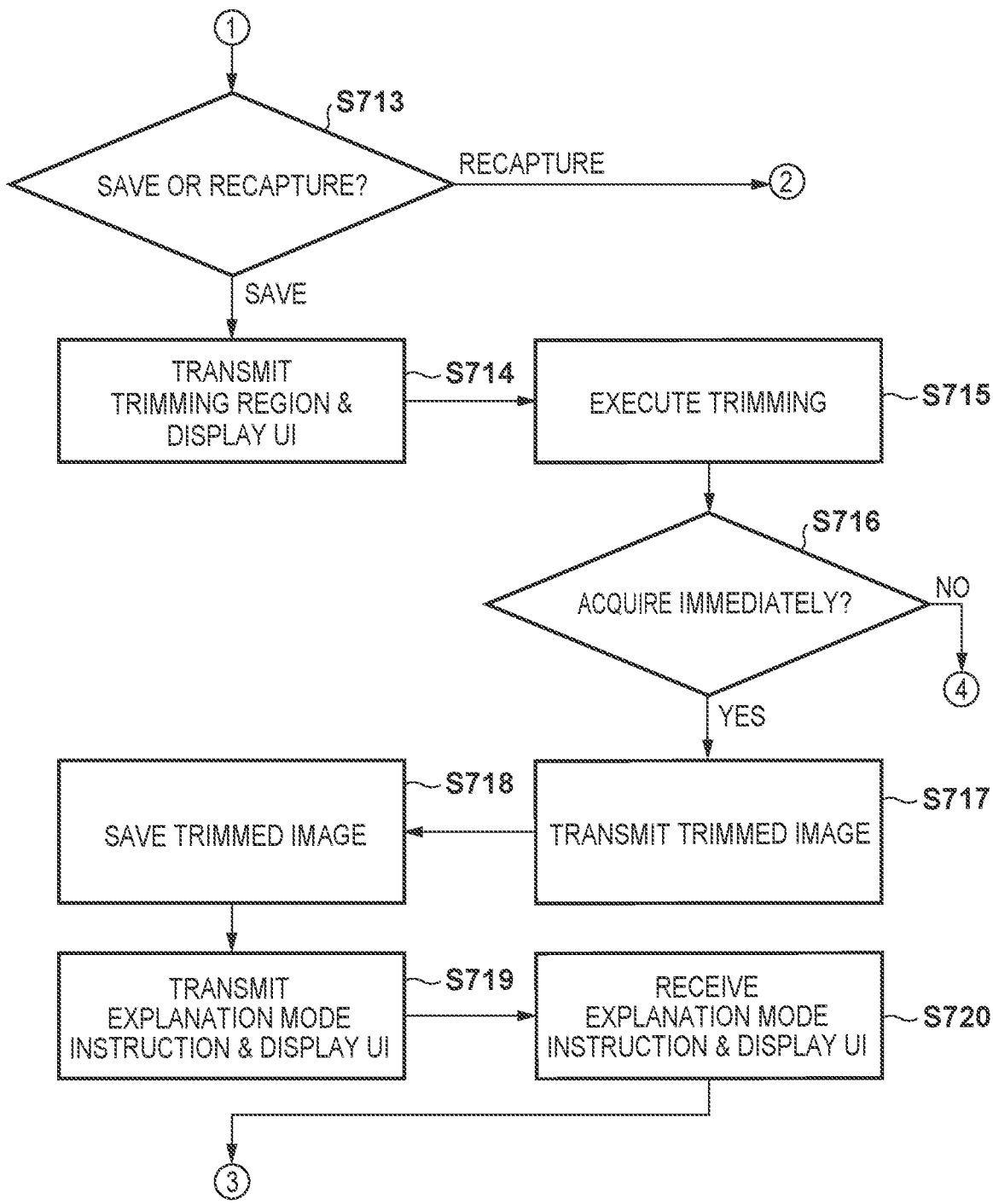
Figure 7C:
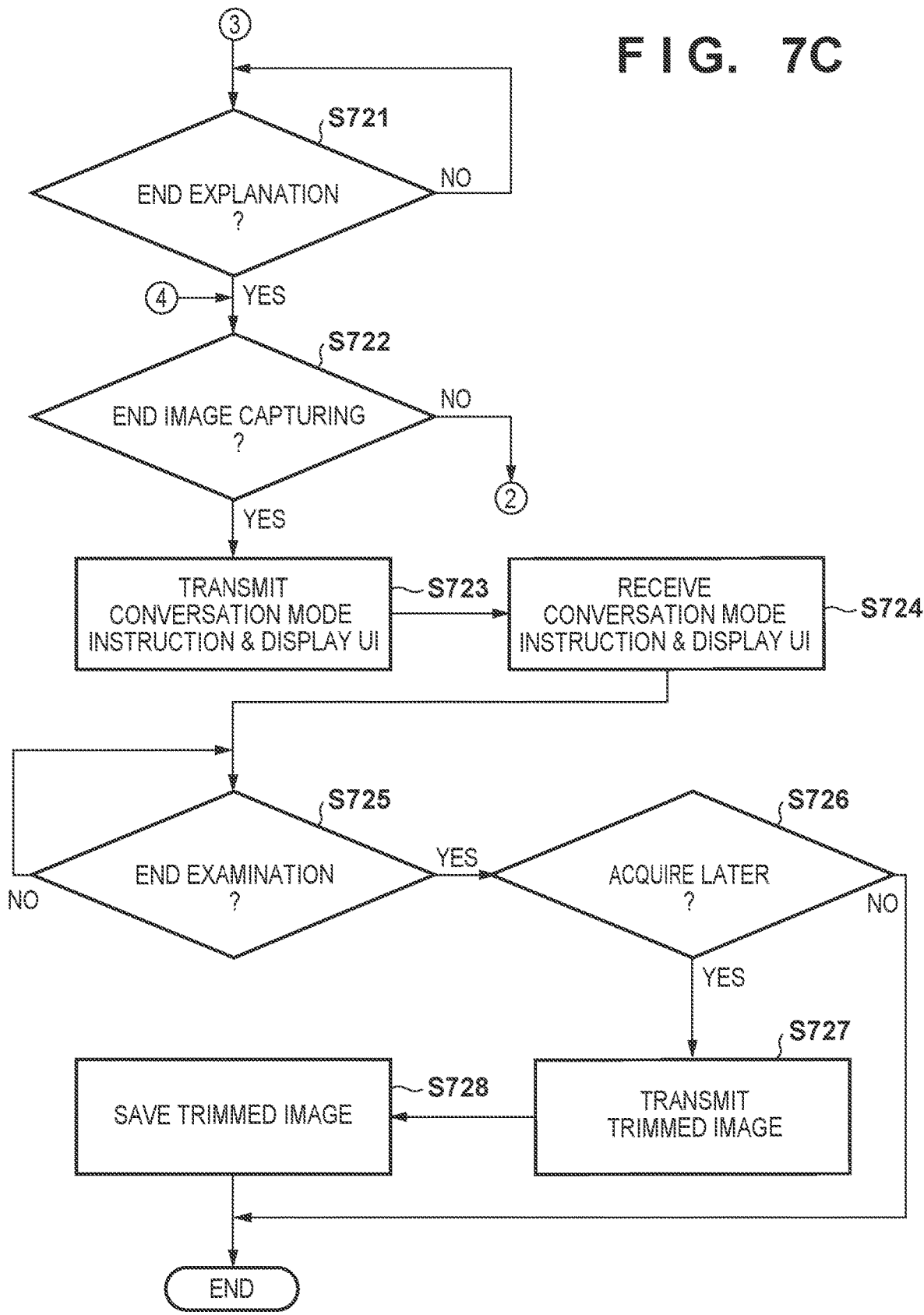

Next, operations of the physician-side information processing apparatus and the patient-side information processing apparatus in the telemedicine system of the present embodiment will be described with reference to FIGS. 7A-7C.

In the storage unit of the physician-side information processing apparatus 101 and the patient-side information processing apparatus 103, data that is related to UIs that correspond to the respective modes (conversation, image capture, trimming, explanation) in the flow of the telemedicine of FIG. 3 is stored.

In step S701, the physician-side information processing apparatus 101 transmits to the patient-side information processing apparatus 103 an instruction for transitioning to a conversation mode. The physician-side information processing apparatus 101 displays, for example, the UI 310 of FIG. 3 on the display 201.

In step S702, the patient-side information processing apparatus 103 receives from the physician-side information processing apparatus 101 an instruction for transitioning to the conversation mode. The patient-side information processing apparatus 103 displays, for example, the UI 312 of FIG. 3 on the display 201.

In step S703, the physician-side information processing apparatus 101 determines whether or not the conversation mode has ended. As described in step S301 of FIG. 3, in the conversation mode, when the physician inputs by voice an instruction for starting image capturing, for example, the physician-side information processing apparatus 101 determines that the voice, which has been acquired by the audio input unit 211, is an instruction for starting image capturing. In addition, as a method other than voice, a configuration may be taken so as to dispose a mode change button in a UI that is displayed on the display 201 and determine that the mode change button has been operated by the PD 205. While the conversation mode of step S703 is being continued, the physician and the patient are communicating with each other as described in step S301 of FIG. 3, for example.

In step S704, the physician-side information processing apparatus 101 transmits to the patient-side information processing apparatus 103 an instruction for transitioning to the image capture mode. The physician-side information processing apparatus 101 displays, for example, the UI 320 of FIG. 3 or the UI 610 or the UI 630 of FIG. 6 on the display 201.

In step S705, the patient-side information processing apparatus 103 receives from the physician-side information processing apparatus 101 an instruction for transitioning to the image capture mode. The patient-side information processing apparatus 103 displays, for example, the UI 322 of FIG. 3 or the UI 631 of FIG. 6 on the display 201.

In step S706, the physician-side information processing apparatus 101 transmits an image capture instruction to the patient-side information processing apparatus 103 in order to capture an image of the patient (diseased part) by the patient-side image capture apparatus 104. Regarding the image capture instruction, it is sufficient to operate the image capture start button 321 of the UI 320 of FIG. 3 by the PD 205, for example.

In step S707, the patient-side information processing apparatus 103 receives from the physician-side information processing apparatus 101 the image capture instruction. The patient-side information processing apparatus 103 performs image capturing of the patient (diseased part) by the patient-side image capture apparatus 104 in response to the image capture instruction and stores the generated image data in the storage unit.

In step S708, the patient-side information processing apparatus 103 generates thumbnail data from the image data (original image data) that has been stored in step S707, stores it in the storage unit, and transmits it to the physician-side information processing apparatus 101. In this case, the file size of the image data (original image) is also transmitted. The file size is the amount of data in the image file. For example, a JPEG image file with 3648×2736 pixels (10 MP, 4:3) will have a file size of approximately 2.9 MB depending on the compression ratio. When generating thumbnail data from this image file, it may be reduced into a JPEG image of 640×480 pixels (0.3 MP, 4:3), for example. The file size is used for calculating the file size of the trimmed original image in step S804, which will be described later in FIG. 8.

In step S709, the physician-side information processing apparatus 101 stores the thumbnail data and the file size of the original image data received from the patient-side information processing apparatus 103 in the storage unit.

In step S710, the physician-side information processing apparatus 101 transmits to the patient-side information processing apparatus 103 an instruction for transitioning to the trimming mode. The physician-side information processing apparatus 101 displays, for example, the UI 330 of FIG. 3 or the UI 410 of FIG. 4 on the display 201.

In step S711, the patient-side information processing apparatus 103 receives from the physician-side information processing apparatus 101 an instruction for transitioning to the trimming mode. The patient-side information processing apparatus 103 displays, for example, the UI 333 of FIG. 3 on the display 201.

In step S712, the physician-side information processing apparatus 101 performs the trimming region designation processing based on the thumbnail data that has been stored in step S709 and the file size of the original image data. The physician-side information processing apparatus 101 can acquire the information of the trimming region of the original image data by converting the coordinate information of the trimming region that has been set on the thumbnail data to the file size of the original image data. Details of the trimming region designation processing will be described later in FIG. 8.

In step S713, the physician-side information processing apparatus 101 determines whether to save the thumbnail data and the file size of the original image data that have been received in step S709 and the information of the trimming region that has been acquired in step S712 or discard them (perform image re-capturing). For example, when the image re-capture button 416 of FIG. 4 is operated, the physician-side information processing apparatus 101 determines that image re-capturing is to be performed, and when the save button 417 of FIG. 4 is operated, the physician-side information processing apparatus 101 determines that saving is to be performed. When the physician-side information processing apparatus 101 determines to perform image re-capturing, the physician-side information processing apparatus 101 starts the processing of step S704, and when the physician-side information processing apparatus 101 determines to perform saving, the physician-side information processing apparatus 101 starts the processing of step S714.

In step S714, the physician-side information processing apparatus 101 transmits information of the trimming region, which has been saved in step S713, to the patient-side information processing apparatus 103. In this case, flag information, which indicates whether or not to immediately acquire the trimmed original image, is also transmitted in accordance with whether or not there is a check in the check box 414 of the UI 410 of FIG. 4. When the transmission is complete, the physician-side information processing apparatus 101 displays, for example, the UI 340 of FIG. 3 on the display 201. The trimmed thumbnail 341 displayed on the UI 340 is generated in the processing for storing information of a trimming region of step S803, which will be described later.

In step S715, the patient-side information processing apparatus 103 executes the processing for trimming image data (original image) based on the information of a trimming region, which has been received from the physician-side information processing apparatus 101. Since the coordinate information of the trimming region designated in step S712 is calculated based on the thumbnail, it is necessary to convert the coordinate information to the size of the image data (original image). In the example of the file size that has been described in step S708, for image data (original image) whose JPEG image is 3648×2736 pixels (10 MP, 4:3), the thumbnail data is a JPEG image of 640×480 pixels (0.3 MP, 4:3), so the trimming region of the image data (original image) can be calculated by vertically and horizontally multiplying by 5.7 the upper left and lower right coordinates of the trimming region that has been received from the physician-side information processing apparatus 101 in step S714.

In step S716, the patient-side information processing apparatus 103 determines whether or not to immediately transmit the trimmed original image to the physician-side information processing apparatus 101 based on the flag information, which has been received from the physician-side information processing apparatus 101 in step S714. When the patient-side information processing apparatus 103 determines that the trimmed original image is to be immediately transmitted, the patient-side information processing apparatus 103 advances the processing to step S717, and when the patient-side information processing apparatus 103 determines that the trimmed original image is not to be immediately transmitted, the patient-side information processing apparatus 103 advances the processing to step S722. When the patient-side information processing apparatus 103 determines that the trimmed original image is not to be immediately transmitted, it will be transmitted in step S727, which will be described later, and therefore is stored in the storage unit.

In step S717, the patient-side information processing apparatus 103 transmits to the physician-side information processing apparatus 101 the trimmed original image that has been generated in step S715. The patient-side information processing apparatus 103 displays, for example, the UI 344 of FIG. 3 on the display 201.

In step S718, the physician-side information processing apparatus 101 stores the trimmed original image received from the patient-side information processing apparatus 103 in the storage unit.

In step S719, the physician-side information processing apparatus 101 transmits to the patient-side information processing apparatus 103 an instruction for transitioning to the explanation mode. The physician-side information processing apparatus 101 displays, for example, the UI 350 of FIG. 3 on the display 201.

In step S720, the patient-side information processing apparatus 103 receives from the physician-side information processing apparatus 101 an instruction for transitioning to the explanation mode. The patient-side information processing apparatus 103 displays, for example, the UI 354 of FIG. 3 on the display 201.

In step S721, the physician-side information processing apparatus 101 determines whether or not the explanation mode has ended. As described in step S305 of FIG. 3, in the explanation mode, when the physician conveys by voice to the patient that they will end the explanation, for example, the physician-side information processing apparatus 101 determines that the voice, which has been acquired by the audio input unit 211, is an instruction for ending explanation. As a method other than voice, a configuration may be taken so as to dispose an explanation end button in a UI that is displayed on the display 201 and when the explanation end button has been operated by the PD 205, determine to end the explanation.

In step S722, the physician-side information processing apparatus 101 determines whether or not to continue image capturing. This makes it possible for the physician to consecutively perform image capturing and explanation of step S706 and later. In the image capture mode, when the physician inputs by voice that they will end capturing the diseased part, for example, the physician-side information processing apparatus 101 determines that the voice, which has been acquired by the audio input unit 211, is an instruction for end image capturing. As a method other than voice, a configuration may be taken so as to dispose an image capture end button in a UI that is displayed on the display 201 and when the image capture end button has been operated by the PD 205, determine to end image capturing.

In step S723, the physician-side information processing apparatus 101 transmits to the patient-side information processing apparatus 103 an instruction for transitioning to the conversation mode. The physician-side information processing apparatus 101 displays, for example, the UI 310 of FIG. 3 on the display 201.

In step S724, the patient-side information processing apparatus 103 receives from the physician-side information processing apparatus 101 an instruction for transitioning to the conversation mode. The patient-side information processing apparatus 103 displays, for example, the UI 312 of FIG. 3 on the display 201.

In step S725, the physician-side information processing apparatus 101 determines whether or not to end the conversation mode (telemedicine). While telemedicine continues, the physician and the patient converse on drugs to be prescribed, questions and answers on the entire examination, the next examination, and the like as described in step S306 of FIG. 3, for example. In the conversation mode, when the physician inputs by voice that they will end telemedicine, for example, the physician-side information processing apparatus 101 determines that the voice, which has been acquired by the audio input unit 211, is an instruction for ending telemedicine. As a method other than voice, a configuration may be taken so as to dispose a telemedicine end button in a UI that is displayed on the display 201 and when the telemedicine end button has been operated by the PD 205, determine to end telemedicine.

In step S726, the patient-side information processing apparatus 103 determines whether or not there is a trimmed original image, which has been stored for later transmission in step S716, based on the flag information received from the physician-side information processing apparatus 101 in step S714. When the patient-side information processing apparatus 103 determines that there is a trimmed original image which has been stored for later transmission, the patient-side information processing apparatus 103 advances the processing to step S727, and otherwise, the patient-side information processing apparatus 103 terminates the processing.

Similarly to step S717, in step S727, the patient-side information processing apparatus 103 transmits to the physician-side information processing apparatus 101 the trimmed original image that has been saved in step S716.

Similarly to step S718, in step S728, the physician-side information processing apparatus 101 stores the trimmed original image received from the patient-side information processing apparatus 103 in the storage unit.

A description has been given assuming that in step S707, the patient-side image capture apparatus 104 can perform image capturing, however, if image capturing cannot be performed, such as in a case of a web camera, image data which is a screenshot of the live view may be generated in response to the image capture instruction and then stored.

<Trimming Region Designation Processing>

Next, the trimming region designation processing in step S712 of FIG. 7A will be described with reference to FIG. 8.

In step S712, the physician-side information processing apparatus 101 displays, for example, the UI 410 of FIG. 4 on the display 201.

In step S801, the physician-side information processing apparatus 101 continues processing as an operation for starting the designation of the trimming region of the thumbnail 411 of the UI 410 of FIG. 4 until the drag operation of the PD 205 on the thumbnail 411 of the UI 410 is detected. Then, if the physician-side information processing apparatus 101 detects the drag operation of the PD 205, the physician-side information processing apparatus 101 advances the processing to step S802. In this case, a start position of the drag operation becomes the upper left coordinates of coordinates of a rectangle of the trimming region. The physician-side information processing apparatus 101 stores the coordinate information of the start position of the drag operation in the storage unit.

In step S802, the physician-side information processing apparatus 101 continues processing as an operation for ending the designation of the trimming region of the thumbnail 411 of the UI 410 of FIG. 4 until an end of the drag operation of the PD 205 on the thumbnail 411 of the UI 410 is detected. Then, if the physician-side information processing apparatus 101 detects the end of the drag operation of the PD 205, the physician-side information processing apparatus 101 advances the processing to step S803. In this case, an end position of the drag operation becomes the lower right coordinates of the coordinates of the rectangle of the trimming region. The physician-side information processing apparatus 101 stores the coordinate information of the end position of the drag operation in the storage unit.

In step S803, the physician-side information processing apparatus 101 temporarily stores the coordinate information of the trimming region that has been stored in steps S801 and S802 and the trimmed thumbnail data in the storage unit. The trimmed thumbnail data that has been temporarily stored here corresponds to the trimmed thumbnail 341 of the UI 340 of FIG. 3, which is displayed on the display 201 of the physician-side information processing apparatus 101 in step S714 of FIG. 7B.

In step S804, the physician-side information processing apparatus 101 converts the coordinate information of the trimming region of the trimmed thumbnail data stored in step S803 into the size of the original image, which is also used in calculating the data transfer time in step S805. Regarding a method of calculation for the size of the trimmed original image, when a description is given using the example of step S708 of FIG. 7A, for an original image that is a 2.9-MB JPEG image of 3648×2736 pixels (10 MP, 4:3), it is assumed that the thumbnail is an 87-KB JPEG image of 640×480 pixels (0.3 MP, 4:3). For example, if the coordinates of the trimming region of the thumbnail stored in step S803 is a rectangle whose start position is (100, 50) and end position is (500, 300), by vertically and horizontally multiplying each by 5.7 as a ratio for converting the image to the size of the original image, the trimmed original image will have the start position (570, 285) and the end position (2850, 1710), and thereby the file size can be calculated to be approximately 944 KB.

In step S805, the physician-side information processing apparatus 101 calculates the data transfer time of the trimmed original image and displays it as the transfer time display 415 of the UI 410 of FIG. 4. Regarding a method of calculation for the transfer time, for example, the transfer time can be calculated from the time that is necessary for transmitting the thumbnail data in step S708 of FIG. 7A and the file size of the original image data. For example, in a case where for an original image that is a 2.9-MB JPEG image of 3648×2736 pixels (10 MP, 4:3), the thumbnail is an 87-KB JPEG image of 640×480 pixels (0.3 MP, 4:3), if the transfer time of the thumbnail (87 KB) is 0.1 seconds, the transfer time of the original image (944 KB) can be calculated to be about 1.1 seconds.

As described above, according to the present embodiment, images and UIs can be displayed without delay or disturbance and smooth communication can be performed in telemedicine that involves image capturing.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-203604, filed Dec. 15, 2021 which is hereby incorporated by reference herein in its entirety.

What is claimed is:

1. A physician-side information processing apparatus that is connected so as to be capable of communicating with a patient-side information processing apparatus, the physician-side information processing apparatus comprising:

a memory containing instructions and a processor to execute the instructions to operate as:

a reception unit that receives from the patient-side information processing apparatus a second image in which a patient has been captured in response to an instruction of the physician-side information processing apparatus and whose data amount has been reduced in comparison to a first image in which the patient has been captured;

a processing unit that performs processing for cutting out a partial image from the second image;

a transmission unit that transmits, to the patient-side information processing apparatus, information that has been set by performing the processing on the second image by the processing unit, wherein the reception unit receives from the patient-side information processing apparatus a processed image that is the first image on which the processing has been performed based on the information in the patient-side information processing apparatus, wherein the physician-side information processing apparatus can be switched between a plurality of modes; and a display unit that displays a user interface that includes the second image and accords with any one of the plurality of modes, wherein the plurality of modes include a first mode in which the patient and a physician converse, a second mode in which an image of the patient is captured, wherein the second mode transitions from the first mode, a third mode in which the processing is performed on an image of the patient, wherein the third mode transitions from the second mode, and a fourth mode in which an explanation is given to the patient using the processed image, wherein the fourth mode transitions from the third mode, and in the second mode, the transmission unit transmits an instruction for capturing an image of the patient to the patient-side information processing apparatus, and in the third mode, the transmission unit transmits the information to the patient-side information processing apparatus.

2. The physician-side information processing apparatus according to claim 1, wherein in the second mode, an image capture instruction unit and a physician-side image are displayed superimposed on the second image, and in the third mode, a patient-side image and a physician-side image are displayed superimposed on the processed image.

3. The physician-side information processing apparatus according to claim 1, wherein the processor calculates a time that is necessary for receiving the processed image from a file size and a transfer speed for when the second image has been received from the patient-side information processing apparatus, wherein the display unit displays the time in the third mode.

4. The physician-side information processing apparatus according to claim 1, wherein the display unit displays a unit that designates a timing at which the processed image is to be acquired from the patient-side information processing apparatus in the third mode, and the timing includes a timing at which the third mode has ended or a timing at which the fourth mode has ended in the physician-side information processing apparatus.

5. The physician-side information processing apparatus according to claim 1, wherein the display unit displays, in the third mode, a unit by which the second mode is returned to and an image of the patient is re-captured, and displays a unit by which the information that has been set in the third mode is saved and the third mode is ended.

6. The physician-side information processing apparatus according to claim 1, wherein the display unit displays, in the second mode, a unit by which whether to capture the patient by a first image capture apparatus that captures a patient-side image or capture the patient by a second image capture apparatus by which a third party other than the patient captures a patient-side image for the patient-side information processing apparatus is selectable, and the display unit is capable of switching between and displaying the image in which the patient has been captured by the first image capture apparatus and the image in which the patient has been captured by the second image capture apparatus.

7. The physician-side information processing apparatus according to claim 1, wherein the display unit replaces the processed second image that is being displayed in the third mode to the processed first image that has been received from the patient-side information processing apparatus.

8. The physician-side information processing apparatus according to claim 1, wherein the second image is a thumbnail that corresponds to the first image, the processing is trimming in which a part of an image is cut out, the information is information of a region on which to perform the trimming.

9. A method of controlling a physician-side information processing apparatus that is connected so as to be capable of communicating with a patient-side information processing apparatus, the method comprising:

receiving from the patient-side information processing apparatus a second image in which a patient has been captured in response to an instruction of the physician-side information processing apparatus and whose data amount has been reduced in comparison to a first image in which the patient has been captured;

performing processing for cutting out a partial image from the second image that is being displayed on the display unit;

transmitting, to the patient-side information processing apparatus, information that has been set by performing the processing on the second image;

receiving from the patient-side information processing apparatus a processed image that is the first image on which the processing has been performed based on the information in the patient-side information processing apparatus, wherein the physician-side information processing apparatus can be switched between a plurality of modes; and displaying a user interface that includes the second image and accords with any one of the plurality of modes, wherein the plurality of modes include a first mode in which the patient and a physician converse, a second mode in which an image of the patient is captured, wherein the second mode transitions from the first mode, a third mode in which the processing is performed on an image of the patient, wherein the third mode transitions from the second mode, and a fourth mode in which an explanation is given to the patient using the processed image, wherein the fourth mode transitions from the third mode, and in the second mode, transmitting an instruction for capturing an image of the patient to the patient-side information processing apparatus, and in the third mode, transmitting the information to the patient-side information processing apparatus.

10. A non-transitory computer-readable storage medium storing a program for causing a processor to function as a physician-side information processing apparatus that is connected so as to be capable of communicating with a patient-side information processing apparatus, the program comprising:

receiving from the patient-side information processing apparatus a second image in which a patient has been captured in response to an instruction of the physician-side information processing apparatus and whose data amount has been reduced in comparison to a first image in which the patient has been captured;

performing processing for cutting out a partial image from the second image;

transmitting, to the patient-side information processing apparatus, information that has been set by performing the processing on the second image by the processing unit;

receiving from the patient-side information processing apparatus a processed image that is the first image on which the processing has been performed based on the information in the patient-side information processing apparatus, wherein the physician-side information processing apparatus is capable of being switched among a plurality of modes; and displaying a user interface that includes the second image and accords with any one of the plurality of modes, wherein the plurality of modes include a first mode in which the patient and a physician converse, a second mode in which an image of the patient is captured, wherein the second mode transitions from the first mode, a third mode in which the processing is performed on an image of the patient, wherein the third mode transitions from the second and a fourth mode in which an explanation is given to the patient using the processed image, wherein the fourth mode transitions from the third mode, and in the second mode, transmitting an instruction for capturing an image of the patient to the patient-side information processing apparatus, and in the third mode, transmitting the information to the patient-side information processing apparatus.

\* \* \* \* \*